United States Patent
Perrott et al.

(12) 
(10) Patent No.: US 6,217,901 B1
(45) Date of Patent: Apr. 17, 2001

(54) LIPOSOME-ASSISTED SYNTHESIS OF POLYMERIC NANOPARTICLES

(75) Inventors: Michael G. Perrott, Wilmington, DE (US); Stephen E. Barry, Oakland, CA (US)

(73) Assignee: Alnis, LLC, Emeryville, CA (US)

( * ) Notice: Subject to any disclaimer, the term of this patent is extended or adjusted under 35 U.S.C. 154(b) by 0 days.

(21) Appl. No.: 09/579,860

(22) Filed: May 25, 2000

Related U.S. Application Data

(60) Provisional application No. 60/135,937, filed on May 25, 1999.

(51) Int. Cl.[7] .................................................. A61K 9/127
(52) U.S. Cl. ...................................... 424/450; 427/213.31
(58) Field of Search ......................... 424/450; 427/213.31

(56) References Cited

U.S. PATENT DOCUMENTS 6,010,681 * 1/2000 Margerum et al. .................. 424/9.38

FOREIGN PATENT DOCUMENTS

WO 99/19276   4/1999   (WO) .

OTHER PUBLICATIONS

Torchilin, V.P., et al. *Makromol. Chem., Rapid Commun.* 8: 457–460 (1987).
Search Report (published Aug. 19, 1999) for WO 99/19276 (see above).

* cited by examiner

*Primary Examiner*—Morton Foelak
(74) *Attorney, Agent, or Firm*—Jacqueline S. Larson

(57) ABSTRACT

Synthetic polymer complements (SPCs) are provided, as well as methods for their synthesis and use. The SPCs range in size from about 20 to about 1000 nm. The SPCs have surfaces that are complementary to surface sites of target molecules, resulting in the ability of the SPCs to selectively bind to molecular targets. The molecular recognition capability of these particles enables their use in diagnostic, therapeutic, and separation applications. The SPC is formed by contacting a target template molecule with a set of building blocks solubilized in the interior of a liposome, which building blocks are then polymerized into a network to form the synthetic polymer complement in the interior of the liposome. The target templates are removed to produce complementary sites in a SPC that map the surface of the target, resulting in a water-soluble SPC nanoparticle of similar dimensions as the interior of the liposome that originally supported it and capable of molecular recognition.

14 Claims, 1 Drawing Sheet

Lipids + Target Templates + SPC Building Blocks
↓ Mix

↓ Polymerize building blocks

↓ Remove lipid and protein to reveal templated SPC

LIPOSOME-ASSISTED SYNTHESIS OF POLYMERIC NANOPARTICLES

RELATED APPLICATIONS

This application claims the benefit of co-pending U.S. Provisional patent application Ser. No. 60/135,937, filed on May 25, 1999, the entire disclosure of which is incorporated herein by reference.

FIELD OF THE INVENTION

This invention relates to the creation of polymer nanoparticles capable of specifically binding to biological molecular targets and to the manufacture of such polymer nanoparticles, enabled through the use of liposomes.

BACKGROUND OF THE INVENTION

Molecular recognition events are ubiquitous in life. Example molecular recognition events include:

The recognition of foreign proteins or foreign biopolymers by soluble antibodies or T-cell receptors.

Pathogen surface molecules binding to cellular receptors (e.g. adhesion molecules) to gain access to the cytoplasm.

The binding of cytokines to cellular receptors. Cytokine binding triggers a wide range of signal transduction events in a cell. For instance in tumor metastasis, angiogenesis and tumor cell proliferation is promoted.

The binding of fibronectin by integrins to affect blood clotting.

Biologically active macromolecules are complex entities that have intricate three-dimensional structures. The exact spatial conformation of these macromolecules is directly related to their biological function. For example, proteins are composed of amino acids in well-defined sequences. Amino acids may have both polar and nonpolar side groups; the polar side groups may in turn be either charged or uncharged in aqueous buffers near neutral or physiological pH.

The three-dimensional structure of a particular polypeptide chain depends on the multiple spatially-specific interactions of its unique sequence, or primary structure. The chain folds into a three-dimensional structure in accordance with the multitude of specific interactions among the constituent amino acid units. For example, there are $10^{26}$ possible primary structures for a 20-amino acid polypeptide. The secondary, tertiary, and quaternary structural possibilities increase the complexity.

Molecular imprinted polymers, or MIPs, have been developed for molecular recognition applications. Molecular imprinted polymers (MIPs) rely on a semi-directed method of forming recognition sites by using the intended target as a template around which monomers assemble. See, (a) Mosbach, K., *Trends Biochem. Sci.*, 19:9–14 (1994), (b) Wulff, G., *Angew. Chem. Int Ed. Engl.*, 34:1812–1832 (1995) (c) Mosbach, K. and Ramström, O; *Biotechnology*, 14:163–170 (1996) and (d) Takeuchi, T. and Matsui, *J. Acta Polymer*, 47:471–480 (1996). MIPs are fabricated by polymerizing monomers (e.g., acrylic acid) and cross-linking molecules (e.g., ethylene glycol diacrylate) in the presence of an "imprinting molecule" to produce a large, rigid, and insoluble polymer structure in which template molecules are embedded. Removal of the template molecules leaves imprints of the template molecule. These molecularly imprinted polymers are then capable of recognizing the molecules that were used as templates. A nonsolvent (e.g., chloroform) "porogen" is employed during polymerization to produce large pores in the bulk material. The porogen is required to allow target diffusion into the insoluble MIP's inner regions, where the large percentage of the imprints are located. MIP structures must be rigid to achieve target recognition. This rigidity is achieved by employing crosslinking molecules that have a high number of crosslinking moieties per molecular weight. Both bulk and suspension polymerization schemes have been employed. Bulk polymerization produces a rigid plastic product the size of the reaction container, while a polymeric sphere on the order of a micrometer in size (a microsphere) is formed through suspension polymerization.

The resulting MIP is a porous macroscopic solid, which is not soluble and, due to its size, settles out of solution. Each MIP has many imprint sites ($10^8$–$10^2$) with widely varying degrees of binding affinity and with only a small fraction of sites accessible to targets. The use of the porogen in the synthesis procedure results in large voids throughout the structure. The voids are intended to allow for diffusion of target molecules into and out of the imprinted sites. However, many sites are still inaccessible.

Unilamellar liposomes are stable microscopic spherical structures consisting of a lipid bilayer surrounding an aqueous core. The lipid bilayer acts as a permeability barrier, effectively separating aqueous solutes inside and outside the liposome. The stability of liposomes has made their use attractive as drug delivery vehicles.

Liposomes are capable of incorporating biomolecules into their lipid bilayer. These biomolecules include membrane-bound proteins (membrane-bound proteins are particularly important in molecular recognition). Such biomoiecules are involved in molecular recognition processes and are thus potential targets of therapeutic and diagnostic materials. Virus surface molecules have also been incorporated into liposomes. Such liposomes have been referred to as "virosomes". Polymerization of water-soluble monomers in the interior of a liposome has been sparsely reported on in the literature. One successful polymerization method was reported by Torchilin, et.al., *Makromol. Chem., Rapid Communication*, 8:457–460 (1987). Polymerization to form a crosslinked particle in the interior of a liposome may be desirable because the liposome can act as a vessel which limits the size of polymer particle.

Thus, the hollow cores of liposomes have been advantageously employed to encapsulate material for a wide variety of purposes, including cosmetic and drug delivery applications. Liposomes have also been used to present membrane-bound macromolecules for diagnostic, drug delivery and drug development applications. Another use of liposomes is to form polymer spheres of nanometer dimensions in the liposome interior. Here we propose to leverage the ability of liposomes to encapsulate molecules and to fix amphiphilic molecules and/or integral membrane proteins at the lipid bilayer to aid in the formation of polymer particles capable of molecular recognition for diagnostic and therapeutic applications.

The manufacture of diagnostic and therapeutic agents, including small molecules, peptides, and monoclonal antibodies that likewise recognize and bind to specific biomolecular targets, is the basis of the pharmaceutical industry. A new class of materials capable of molecular binding to a broad range of therapeutically and diagnostically important targets could find widespread use.

SUMMARY OF THE INVENTION

The present invention is directed to a method for producing polymer particles, here called Synthetic Polymer Complements ("SPCs") ranging in size from 20 to 1000 nm. The SPCs have surfaces that include functional groups that are complementary to surface sites of target molecules, resulting in the ability of the SPCs to selectively bind to molecular targets with high affinity. The molecular recognition capability of these particles enables their use in diagnostic, therapeutic, and separation applications.

The invention provides a method for the assembly of reactive monomers or building blocks, in a manner that at least partially encapsulates "template" molecules. Polymerization followed by template removal yields the SPC particle structure with molecular recognition sites on its surface. The SPC is then capable of selectively binding to "target" molecules when presented with the target molecule in a mixture of molecules. As used here, "templates", "target templates", and "targets" refer to the same molecular structure. The terms "template" and "target template" are used when discussing the SPC fabrication process; the term "target" is used for example when discussing the SPC in its end-use application.

Essentially, SPCs of the present invention are formed in the interior of liposomes. The SPC is formed by bringing an aqueous solution of building blocks (also referred to herein as a "building block set") into contact with lipid constituents and with target template molecules. At least some of the building blocks have moieties that are complementary to moieties on the target templates, so that the building blocks self-assemble around the target template molecule. Liposomes are formed, and the building blocks within the liposomes are then polymerized to form a network that at least partially surrounds the target templates, the network having a complementary surface to a portion of the surface of the target template. Removal of the lipid bilayer and the target template produces a cavity in a SPC that maps the surface of the target. The cavity will retain its three-dimensional shape after the template is removed. A water-soluble SPC sphere of the same dimensions as the liposome that contained it is produced and is capable, in subsequent solutions in which the target is present, of molecular recognition.

In one embodiment of the invention, the building block set, the lipids and the target template molecules are all added together and liposomes are then formed. In another embodiment of the invention, liposomes are formed from the building blocks and the lipids, and the template molecules are added thereafter. In a third embodiment of the invention, liposomes are formed with the template molecules prior to the addition of the building block set.

Thus, there is provided a method of making a synthetic polymer complement (SPC), the method comprising forming a liposome, wherein a building block set is solubilized in the interior of the liposome; contacting the liposome with at least one target template; allowing the building blocks of the building block set to contact at least a portion of the target template; and polymerizing the building blocks to form a SPC. Optionally, the target template is then removed from the SPC.

The use of liposomes accomplishes two things. First, building blocks are compartmentalized in the liposome core before polymerization. Thus, the liposome size regulates the size of the SPC after polymerization. Second, the liposomes incorporate the lipid-soluble portion of template biomolecules (such as membrane-bound proteins, including virus surface proteins, bacteria surface proteins, tumor cell associated membrane proteins, g-protein coupled receptors (e.g. serotonin receptors), and the like) into their bilayers. Also, soluble proteins that have been chemically modified to produce an amphiphilic structure can be used in the formation of SPCs. The SPCs thus formed are then capable of recognizing and binding to the soluble protein. Thus, liposomes present template molecules in an orientation advantageous for the assembly of SPC building blocks around the target templates.

Provided in one embodiment are compositions comprising SPCs, in a pharmaceutically acceptable carrier. Pharmaceutical carriers suitable for a particular route of administration may be used. Exemplary routes of administration include orally, parenterally, topically, by inhalation, by implantation, intravenously, mucosal delivery, dermal delivery, and ocular delivery. The SPC and/or target may be formulated into appropriate forms for different routes of administration as described in the art, for example, in "*Remington: The Science and Practice of Pharmacy*", Mack Publishing Company, Pennsylvania, 1995, the disclosure of which is incorporated herein by reference.

DETAILED DESCRIPTION OF THE INVENTION

Figure 1A:
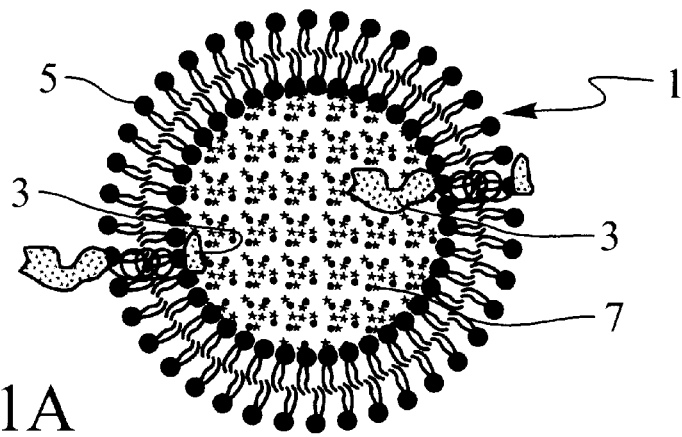
FIG. 1 illustrates a reaction scheme for the preparation of the SPCs of the invention.

The terms "a" and "an" mean "one or more" when used herein.

Provided are compositions for forming SPCs comprising the building blocks and lipid materials, SPCs, and SPC use. In this invention, liposomes are used to aid in the formation of SPC structures. The liposome is capable of incorporating one to about 10,000, and preferably from about 10 to about 1000 template molecules into its lipid bilayer. After formation, the SPC is an approximately spherical particle with a diameter of between about 20 nm and about 1000 nm and having a plurality of sites on its surface capable of specifically recognizing and selectively binding about 1 to about 10,000 molecules of the target.

To form the SPC, building blocks are solubilized at about 5 wt % to about 50 wt % in the interior of a liposome. The target template molecules are located at the lipid bilayer of the liposome. Subsequently, reactive groups on the building blocks are crosslinked, forming the synthetic polymer complement (SPC). The polymer surface next to the template molecules is complementary to the template surface. After the template molecules are removed, in subsequent solutions the SPCs are capable of specifically binding to the same molecules, or fractions of the same molecules, or molecules consisting in part of the same molecules that were used as template molecules.

Building Blocks

Building blocks can have a monomeric, oligomeric, or polymeric structure. Building blocks are generally hydrophilic water-soluble compounds. At least a portion of the building blocks are comprised of i) moieties that are complementary to template surface moieties and are thus capable of undergoing a binding interaction with a target, preferably with high affinity, and ii) crosslinking moieties that allow the building blocks to be covalently crosslinked to one another. In the practice of the invention, building blocks are usually utilized as building block sets.

Building Block Sets

The building block set may include, for example, one to about 10,000 building blocks. A set may include at least about 2 to about 50, e.g. about 5 to 20, different types of building blocks. The building block set must be water-soluble for incorporation into the liposome core. The building block set must not disrupt the structure of the liposome to the extent that the production of nanoparticles is substantially hindered. Disruption of the liposome bilayer may occur if the building block set is either too "organic", i.e. has a hydrophobic character, or too surface-active in nature. In this case, the lipids will not self-assemble in a bilayer, but will instead be somewhat soluble in the aqueous building block solution. Also, to prevent building blocks from leaking out of the liposome core prior to crosslinking, the time scale for building blocks to diffuse through the lipid bilayer should be slow compared to the time scale of SPC fabrication.

Building block sets comprising specific building blocks may be used in forming a synthetic polymer complement for a particular target. The building blocks in the set may be identical. Alternatively, a variety of different building blocks with the same crosslinking group may be provided in the set. In another embodiment, the crosslinking groups in a set may be the same or different.

In one preferred embodiment, the building block set includes a plurality of different building blocks, having the same crosslinking group. The set may include two, or optionally three or more different types of building blocks (that is, building blocks with different complementary moieties). More complex sets may be designed which have about 4–6, or about 7–10 different types of building blocks, or optionally about 10–20, or 20 or more different building blocks, each building block having different chemical moieties. The selection and ratio of building blocks in a set may be designed selectively for a particular target.

The types, number and relative amounts of the building blocks in a set thus can depend on the nature of the target. For example, if the target has a high density of negative charges, the building block set may include a large number of positive charges on building blocks, and vice versa. Additionally, hydrogen bond donors on the target would require complementary hydrogen bond acceptors on the building block. An important consideration in the selection of the building blocks in a particular set is the diversity needed to effectively map the regions of interest on the target surface. As an example, most protein surfaces are heavily populated with charged residues such as lysine ($R-NH_3^+$) or arginine ($R-C(NH_2)_2^+$). Thus, the building blocks are in one embodiment provided with anionic counterparts such as carboxylates ($R-CO_2^-$) and sulfates ($R-SO_3^-$). Anionically-charged protein surface residues such as glutamate ($R-CH_2-CH_2-CO_2^-$) or aspartate ($R-CH_2-CO_2^-$) are complexed by complementary cationic groups such as ammonium ($R-NR_3^+$) or amidines ($R-C(NR_2)_2^+$).

Example Building Blocks

Exemplary monomeric building blocks include acrylamide, sodium acrylate, methylene bisacrylamide, ammonium 2,2-bisacrylamidoacetate, N-ornithine acrylamide sodium salt, N-ornithine diacrylamide, N-acryloyltris-(hydroxymethyl)methylamine, hydroxyethylacrylate, N-(2-hydroxypropyl)acrylamide, 2-sulfoethylmethacrylate, 2-methacryloylethyl glucoside, glucose monoacrylate, glucose-1-(N-methyl)acrylamide, glucose-2-acrylamide, glucose-1,2-diacrylamide, maltose-1-acrylamide, sorbitol monoacrylate, sorbitol diacrylate, sucrose diacrylate, sucrose mono(ethylenediamine acrylamide), sucrose di(ethylenediamine acrylamide), sucrose di(diethylenetriamine acrylamide), kanamycin tetraacrylamide, kanamycin diacrylamide, dextran multiacrylamide, sucrose mono(ethylenediamine acrylamide) mono(diethylenetriamine acrylamide) mono(phenyl alanine) sodium salt, as well as other acrylate- or acrylamide-derivatized sugars.

Oligomeric and polymeric building blocks may be advantageously employed to produce a more stable pre-polymerized liposome complex. By employing polymeric building blocks with many copies of a given moiety, the entropy loss of assembling many monomers around a target is avoided. More favorably, one or a few multifunctional polymeric building blocks are assembled around the target. Also, the strength of the interaction of the multi-functional polymer by binding multiple sites on a target is much more stable than monomeric interactions. Another advantage of polymeric building blocks is that, compared to lower molecular weight building blocks, there will be reduced leakage rates of the building blocks from the liposome interior (lower lipid bilayer permeability due to higher molecular weight). Example acrylate-functionalized polymeric building blocks include polyethyleneglycol diacrylate, chitosan with a range of acrylamide moieties, and dextran ranging in size from approximately 500 to 40,000 daltons and functionalized with a range of acrylate or acrylamide moieties and molecular weights. Building blocks based on modified polysaccharides such as acrylated dextran, for example, are easy to synthesize, have excellent water solubility, and may be easily degraded by the body.

Building blocks derived from small molecules, peptides or proteins may also be advantageously employed. The recognition portion (or complementary moiety) can vary from 6 to 50 amino acids. Preferably, the recognition portion ranges from 6 to 15 amino acids, and most preferably from 6 to 10 amino acids. Building blocks comprised of moieties that are known to be recognized by target templates can be employed. Such building blocks include small molecules such as NSAIDS, peptides such as that comprising the arginine-glycine-aspartic acid (RGD) peptide sequence, and monoclonal antibodies.

In one embodiment, the building block includes i) at least one functional group or moiety (a "complementary moiety"), capable of a preferably non-covalent binding interaction with a site on the target template, and ii) a crosslinking group, which is a reactive group, capable of undergoing a covalent reaction with another of the building blocks. The crosslinking group preferably permits crosslinking and/or polymerization of the building blocks under certain conditions. For some building blocks, the portion of the molecule that serves as a recognition element may not be readily identifiable. Rather, the entire building block may be seen as interacting with the template molecule moieties.

Building block complementary moieties include polar or nonpolar moieties. Polar moieties for interaction with a particular target may be negatively charged, positively charged, or uncharged. Nonpolar moieties include bulky, sterically small, rigid, flexible, aliphatic and/or aromatic moieties. Uncharged polar moieties include hydrogen bond-forming or non-hydrogen bond-forming functional groups. Hydrogen bond-forming moieties include hydrogen bond donors or acceptors.

Exemplary moieties include alcohols, phenols, carboxylic acids, carboxylates, amides, amines, phosphates, phosphonates, sulfonates, succinates, aromatic groups including aromatic amines, ammonium salts, amidine salts, aliphatic groups, sugars, disaccharides and polysaccharides. Additional useful moieties may be naturally occurring or synthetic. For example, the building block complementary moiety may be a naturally occurring amino acid, an amino acid side chain, or a synthetic amino acid derivative. The building block can also comprise a dimer, trimer, or oligomer of the same or different amino acid or derivative thereof. Other exemplary building blocks are comprised of sugars, carbohydrates, and small or large glycoproteins. Still other exemplary moieties include purines or pyrimidines, such as adenine, cytosine, guanine, and thymine.

A consideration in the selection of the building block components of a building block set is diversity to adequately map the regions of interest on the target surface. For example, moieties of varying size, electronegativity, hydrogen-bonding tendency, hydrophobicity, etc., can be chosen. The quantitative representation of components in a building block set can also be optimized for a particular complementary interaction.

Exemplary crosslinking groups include, but are not limited to, acrylate, acrylamide, vinyl ether, epoxide, maleic acid derivative, diene, substituted diene, thiol, alcohol, amine, hydroxyamine, carboxylic acid, carboxylic anhydride, carboxylic acid halide, aldehyde, ketone, isocyanate, succinimide, carboxylic acid hydrazide, glycidyl ether, siloxane, alkoxysilane, alkyne, azide, 2'-pyridyldithiol, phenylglyoxal, iodo, maleimide, imidoester, dibromopropionate, and iodacetyl.

Preferred crosslinkable functionalities are acrylate and acrylamide moieties. Such moieties are amenable to free-radical polymerization. Free-radical polymerization can be readily achieved through the combination of UV light and photoinitiators, redoxcoupled free-radical initiators, or heat and heat-activated initiators.

The number of crosslinking groups attached to one single building block can range, for example, from about one to five for low molecular weight building blocks, to several hundred for polymeric building blocks. Using different amounts of building blocks from a set of building blocks with one, two, or more crosslinkable groups allows formation of synthetic polymer complements in the form of networks of different tightness and topology upon crosslinking of the building blocks.

In one embodiment, there is provided a carbohydrate building block that comprises a carbohydrate region, comprising plural hydroxyl groups, wherein at least one hydroxyl group is modified to include at least one crosslinkable group. In another embodiment, at least one of the hydroxyl groups is modified to include at least one other functionality. In a further embodiment, at least one of the hydroxyl groups is modified to include at least one crosslinkable group and at least one other functionality.

The carbohydrate region of the carbohydrate building block may include a carbohydrate or carbohydrate derivative. For example, the carbohydrate region may be derived from a simple sugar, such as glucose, ribose, arabinose, xylose, lyxose, allose, altrose, man nose, gulose, idose, galactose, fructose or talose; a disaccharide, such as maltose, sucrose or lactose; a trisaccharide; or a polysaccharide, such as cellulose, glycogen and dextran; or modified polysaccharides. Other carbohydrates include sorbitan, sorbitol, and glucosamine. The carbohydrate may include amine groups in addition to hydroxyl groups, and the amine or hydroxyl groups can be modified to include a crosslinking group, other moieties, or combinations thereof.

Procurement of Building Blocks

The building blocks may be synthesized using methods available in the art of organic chemistry without undue experimentation (see, for example, J. March, *Advanced Organic Chemistry*, Fourth Ed., John Wiley and Sons, New York, Part 2, pp. 255–1120, 1992). For example, building blocks can be functionalized with crosslinking and ionic moieties using standard organic reactions, such as ester, amide, or ether linkage formation.

Carbohydrate-based building blocks may be prepared from the carbohydrate precursor (e.g. sucrose, sorbital, dextran, etc.) by standard coupling technologies known in the art of bioorganic chemistry (see, for example, G Hermanson, *Bioconiugation Techniques*, Academic Press, San Diego, pp 27–40, 155, 183–185, 615–617, 1996; and S. Hanesian, *Preparative Carbohydrate Chemistry*, Marcel Dekker, New York, 1997.) For example, a crosslinkable group is readily attached to a carbohydrate via the dropwise addition of acryloyl chloride to an amine-functionalized sugar. Amine-functionalized sugars can be prepared by the action of ethylene diamine (or other amines) on 1,1'-carbonyldiimidazole-activated sugars. Carbohydrate-based building blocks may also be prepared by chemoenzymatic methods (Martin, B. D. et. al. Macromolecules 1992, 25, 7081), in which *Pseudomonas cepacia* catalyzes the transesterfication of monosaccharides with vinyl acrylate in pyridine.

Reagents and starting materials in some embodiments can be obtained commercially. For example, amino acids and purines and pyrimidines can be purchased from chemical distributors such as Aldrich (Milwaukee, Wis.), Kodak (Rochester, N.Y.), Fisher (Pittsburgh, Pa.), Shearwater Polymers (Huntsville, Ala.), Pierce Chemical Company (Rockford, Ill.) and Carbomer Inc. (Westborough, Mass.). Monomers and monomer precursors are also available commercially from Sigma Chemical Company (St. Louis, Mo.), Radcure (Smyrna, Ga.), and Polysciences (Niles, Ill.). Additionally chemical product directories and resources such as <hftp://www.chemdex.com> and <http://pubs.acs.org/chemcy/> may be used to locate starting materials.

Targets

Synthetic polymer complements (SPCs) may be formed with a binding affinity, for example with a specific binding affinity, for any of a variety of targets. The target may be a small molecule, e.g., with a size (i.e. hydrodynamic radius) less than 1 nm, or preferably a macromolecule, such as a protein with a size up to and greater than 10 nm. Example small molecules include organic compounds, toxins, pollutants, synthetic drugs, steroids and derivatives. Preferable is a biological macromolecule such as a peptide or a protein, glycoprotein, polysaccharide, lipopolysaccharide, or polyanion, including nucleic acids. The target may be a molecule, or a portion of a molecule, such as the Fc region or the epitope portion of an antibody. Biological molecules that function as cellular receptors, antibodies, antigens, cytokines, and enzymes may be targets.

The target may be any of a range of different synthetic or naturally occurring polymers, including proteins such as enzymes and antibodies and glycoproteins. The terms "protein", "polypeptide", and "peptide" are used interchangeably herein to refer to polymers of amino acids of any length. The polymer target may be polar or nonpolar, charged or uncharged. The polymer target may be linear, branched, folded, or aggregated. It may comprise modified amino acids, and it may be interrupted by non-amino acids. It also may be modified naturally or by intervention; for example, disulfide bond formation, glycosylation, myristylation, acetylation, alkylation, phosphorylation or dephosphorylation. Also included within the definition are polypeptides containing one or more analogs of an amino acid (including, for example, unnatural amino acids) as well as other modifications known in the art.

The target may be any of a variety of active agents, including pharmaceutical agents, biological modifiers, or diagnostic agents. Detailed parameters and discussions of active agents can be found, for instance, in the *Physician's Desk Reference* (1995) 49th Ed., Medical Economics Data Production Co., New Jersey.

The chemical structures of active agents include, but are not limited to, lipids, organics, proteins, synthetic peptides, natural peptides, peptide mimetics, peptide hormones, steroid hormones, D amino acid polymers, L amino acid polymers, oligosaccharides, polysaccharides, nucleotides, oligonucleotides, nucleic acids, protein-nucleic acid hybrids, antigens and small molecules, as well as cells, tissues, cell aggregates, cell fragments. Combinations of active agents may be used. Saccharides, including polysaccharides, such as heparin, can also be included.

Proteins may be obtained, for example, by isolation from natural sources or recombinantly. Exemplary proteins include, but are not limited to ceredase, calcitonin, erythropoietin, enzymes, biopharmaceuticals, growth hormones, growth factors, insulin, monoclonal antibodies, interferons, interleukins, collagen and cytokines. Enzyines include proteases, DNAses and RNAses.

Suitable steroid hormones include, but are not limited to, corticosteroids, estrogen, progesterone, testosterone and physiologically active analogs thereof. Suitable nucleic acids include, but are not limited to, DNA, RNA and physiologically active analogs thereof.

Specific examples of active agents are listed in U.S. patent appln. Ser. No. 09/172,921, the entire disclosure of which is incorporated herein by reference.

Provided in one embodiment are compositions comprising SPCs in a pharmaceutically acceptable carrier. Pharmaceutical carriers suitable for a particular route of administration may be used. Exemplary routes of administration include orally, parenterally, topically, by inhalation, by implantation, intravenously, mucosal delivery, dermal delivery, and ocular delivery. The SPC, with or without a target, may be formulated into appropriate forms for different routes of administration as described in the art, for example, in *Remington: The Science and Practice of Pharmacy*, Mack Publishing Company, Pennsylvania, 1995, the disclosure of which is incorporated herein by reference.

Overview of SPC Nanoparticle Formation Using Liposomes

Figure 1B:
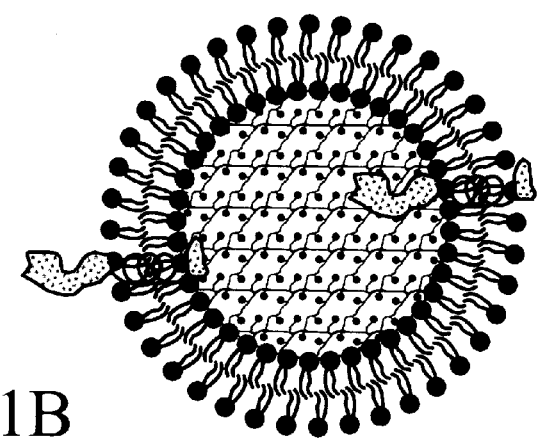
Figure 1C:
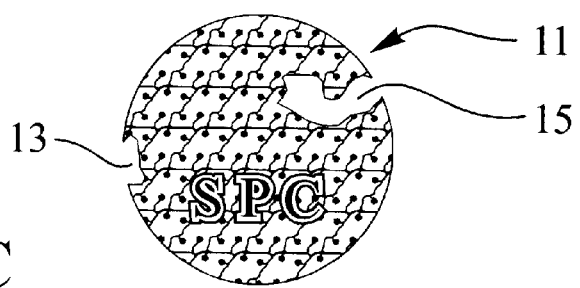

FIG. 1 is a reaction scheme showing the preparation of a SPC of the present invention. Lipids, SPC building blocks, and target templates are mixed together to form, as illustrated in FIG. 1A, a liposome 1 having target templates 3 incorporated into the lipid bilayer 5 of the liposome, the lipid bilayer surrounding and enclosing an aqueous solution containing water-soluble SPC building blocks 7. The building blocks are then polymerized, following standard polymerization procedures, as shown in FIG. 1B. The lipid bilayer and the target templates are thereafter removed to give a water-soluble SPC nanoparticle 11 of the same dimensions as the liposome that contained it and having two cavities 13, 15 that map the surface of the target templates. The resulting SPC has surfaces in the cavities 13, 15 that include functional groups that are complementary to surface sites of the target molecules, resulting in the ability of the SPC to selectively bind to the targets. Although two target templates and two cavities are illustrated in FIG. 1, the invention is not so limited. It is contemplated that from 1 to about 10,000, preferably about 10 to about 1000, recognition sites may be present on the SPC, to selectively bind to from 1 to about 10,000 (preferably about 10 to about 1000) target molecules, which target molecules may be the same or different.

Detailed Description of Nanoparticle Formation Using Liposomes

Liposomes are formed in an aqueous solution containing water-soluble SPC building blocks. The building blocks must not inhibit the formation of the lipid bilayer. This can be accomplished by using highly water-soluble building blocks, and by producing a highly hydrophilic polymer product.

Liposomes can generally be formed from an aqueous solution containing building blocks and lipids by methods well known to those practiced in the art. A detailed discussion of various liposome forming methods is given in *Liposomes: a Practical Approach*, R. R. New, Ed., Oxford University Press, New York, 1990. Such methods include sonication, extrusion, detergent depletion, and reverse phase evaporation.

Liposome Formation

In one embodiment, liposome formation may proceed as follows. The lipid constituents are solvated in an organic solvent such as diethyl ether or chloroform. Evaporating off the organic solvent in a round bottom flask then forms a lipid film. The aqueous building block solution can then be introduced to the flask and, with stirring, liposomes are formed. This solution can contain the membrane-bound protein (the target template), or the protein can be added in an ensuing step. A broad size dispersion of liposomes is produced in this manner. Extrusion of this liposome solution can be used at this point to re-size the liposomes to well-defined diameters.

Lipids that may be employed for liposome formation are those generally used in the art and include, but are not limited to, phosphatidyicholines, phosphatidylserines, phosphatidylg lycerols, phosphatidylethanolamines, phosphatidylinositol, sphingophospholipids, sphingoglycolipids, as well as synthetic lipids. Mixtures of the lipids, as well as additional components that reside in the bilayer, such as cholesterol, phosphatidyl choline, and single-chain detergents such as sodium dodecyl sulphate, may be employed. All the above are included under the term "lipid constituents" herein. Single chain detergents are known to aid in the inclusion of membrane-bound proteins to the lipid bilayer (*Liposomes: From Physics to Applications*, D. Lasic, Elsevier, Amsterdam, 1994).

Also, PEG (polyethylene glycol) phospholipid conjugates, such as PEG-DPPE (polyethylene glycol dipalmitoylphosphatidylethanolamine) may be employed as an additional lipid constituent of the liposome. The use of PEG-DPPE (or other PEGylated lipids) is specialized, in that it will aid in template removal. Depending on the size and shape of the target, it may be completely encased in the polymer matrix after polymerization. The use of PEGylated lipids will create a buffer region between the reactive building blocks and the lipid bilayer surface. In one embodiment of the invention, 5 mole percent of the total lipid in the bilayer is PEGylated lipid; however, PEGylated lipid content may range from 0–20 mole percent.

An alternative way to locate lipid bilayer-bound target templates in the liposome prior to polymerization is to form liposomes with the target template, but not in the presence of the building blocks. This method may be advantageous in some systems because the target template materials may be incorporated into liposomes during target purification steps. The separation and purification of membrane-bound proteins (the target templates) from the cellular mass, followed by reconstitution into liposomes is well described in the art. Typically, a detergent such as octylglycoside, octethyleneglycol dodecyl monoether ($C_{12}E_8$), tetraethyleneglycol octyl monoether $C_8E_4$, or Triton X100 (chemically octylphenol poly(ethyleneglycoether)), is used with an amphiphilic protein to aid in aqueous dissolution and to aid in liposome incorporation (D. Lasic, *Liposomes*, pp. 244–247, supra). Individual liposome structures comprising both the target template and building blocks can then be obtained by extruding a mixture of a liposome-building block solution and liposomes containing target templates. Alternatively, the detergent/protein complex may be added during the liposome-building block formation.

The lipid bilayer of a liposome provides an excellent format for locating an amphiphilic target template at the surface of a building block solution. Targets amenable to incorporation into the lipid bilayer are precisely those that are important as diagnostic and therapeutic targets. That is, eukaryotic cellular surface receptors, such as those important for signal transduction events in tumor cell metastasis, pathogen entry, metabolism, wound healing, immune response, neurotransmission, osteoporosis, rheumatoid arthritis, as well as many other biological and physiological events, are naturally located at lipid bilayers. Generally, eukaryotic transmembrane proteins, apolipoproteins, lipid-linked proteins, lipopolysaccharides, and gram-negative bacteria receptor proteins and endotoxin may be directly incorporated into the lipid bilayer. Other ligands that may be used as templates include antibodies, cytokines, peptides, glycoproteins, and pathogen toxins. Hydrophilic biomolecules with low surface activity can be presented at the liposome surface by attachment of a hydrophobic "anchor". One possible chemical modification method is to functionalize the biomolecule with a hydrophobic tail. As an example, a method well known to those skilled in the art is the reaction of a surface amine on a soluble protein (for example the amine terminus or the primary amine of a lysine residue) with an activated ester on a molecule that also is comprised of one or more hydrophobic tails (see for example, *Bioconjugate Techniques*, G. T. Hermanson, pp. 556–570).

After liposome formation, there are building blocks both inside and outside the liposomes. To prevent polymerization outside of the liposome, building blocks are removed from outside the liposome, for example by running the liposome solution through a gel permeation chromatography (GPC) column. The liposome structure is preserved by eluting the column with a nonreactive solution with an osmolality equal to or greater than the interior of the liposome. Using a solution with greater osmolality (higher solute concentration) will result in the dehydration of the liposome interior. The osmotic potential of the eluting solvent can be controlled through the concentration of solutes such as glucose or sodium chloride. After elution, the building block solutions contained in the liposomes can be polymerized.

Crosslinking of the building blocks in the liposome interior can be initiated using standard polymerization procedures well known to those of ordinary skill in the art (see, for example, Odian G. G.; *Principles of Polymerization*, $3^{rd}$ Ed., Wiley, New York, 1991). For instance, if reactive groups amenable to free-radical polymerization, such as acrylates and acrylamides, are used, polymerization can be induced through the combination of UV initiators and UV light. Generally, solubility decreases as polymerization proceeds. Thus, precipitation and, perhaps, liposome destruction can occur should the water solubility of the forming SPC decrease too much, and care should be taken in choosing building blocks. If the SPCs are to be used internally as therapeutics, they should be degradable in the body to benign materials. The materials should degrade on a time scale consistent with efficacious therapy. If the SPCs are to be used industrially for separation/purification applications, they should be engineered to be robust and resistant to degradation (i.e., fewer amide and ester linkages).

Removal of the Lipid Bilayer and Release of the Target Template

After the assembled building blocks are crosslinked to form the SPC, it is necessary to remove the lipid molecules surrounding the polymerized SPC. The target template is also released in this step or subsequently released, and the SPC is isolated.

The lipid molecules can be removed through the use (singularly or in combination) of surfactant-adsorbing beads, dialysis, solvent washing, or the use of aqueous systems such as 4M urea. Methods for lipid removal are known in the art.

To release a target template, the interactions that were exploited in assembling the superstructure may be dampened or reversed, or the target's morphology may be altered. This can be implemented by, for example, altering the pH, the ionic strength, the solvent or the temperature of the template-SPC complex. Electrostatic interactions can be dampened by increasing the ionic strength. Altering the pH, using urea, or raising the temperature all can be used to alter the charge and charge distribution of a target such as a biomolecule, or to denature a template protein. With these changes, the noncovalent interactions between the template and the SPC are disrupted, causing the template to be released. Alternatively, proteases that will digest or break down a peptide target may be added to the solution. Conditions are selected such that the SPC remains essentially undamaged. For example, the SPC may have enhanced stability due to its covalently crosslinked and hydrolytically-stable chemical structure.

Detachment of the template can be facilitated by slightly swelling or deswelling the synthetic polymer complement, induced by minor adjustment of the co-solvent medium or system temperature. Crosslinked networks undergo volumetric transitions, triggered by small changes in the environment, e.g., temperature, pH, ionic strength, co-solvent composition, pressure, and electric field, etc., as discussed, for example, in L. H. Sperling, *Introduction to Physical Polymer Science*, Chapter 4, pp. 97–121, John Wiley and Sons, New York, 1986.

The following examples are provided to illustrate the practice of the present invention, and are intended neither to define nor to limit the scope of the invention in any manner.

EXAMPLES

Example 1

12 Milligrams of a 2:1 weight mixture of the lipid L-phosphatidylcholine to cholesterol is dissolved in 3 mL diethyl ether and then rotary evaporated on the sides of a flask or vial to remove the ether. The target template is linked to the lipid bilayer using 0.005 mg of the phospholipid, N-(biotinyl)dipalmitoyl-L-α-phosphatidylethanolamine (biotin-DPPE), purchasable from Pierce Chemical Company (Rockford, Ill.). Thus, biotin-DPPE is incorporated into the bilayer along with the other phospholipids. To this lipid film is added 1 mL of a building block set formulation consisting of 15 wt. % sorbitol acrylate and 6.2 wt. % bis-acrylamido acetate (BM), as well as 0.07 wt. % of 4,4'-azobis(4-cyanovaleric acid) (CVA) as the photoinitiator, in a 0.1M sodium phosphate, 0.15M sodium chloride buffer (PBS) pH 7.2. Also present in the building block set solution is one mg of avidin, as the target template. The avidin will bind to the exposed biotin moieties.

The resulting mixture is agitated to disperse the lipids. Under these conditions, liposomes are spontaneously formed, but to ensure equal partitioning of building blocks on both sides of the bilayer the solution is frozen rapidly in liquid nitrogen and thawed several times, which fractures and opens the bilayer for equilibration. The liposomes are then extruded through a 100 nm membrane several times to create a population of liposomes of a very uniform, 100 nm size. The solution is passed through a PD-10 protein-desalting column (Amersham Pharmacia Biotech, Piscataway, N.J.), and is eluted with an isoosmolar glucose solution to replace the untrapped building block solution outside of the liposomes with an isoosmolar non-reactive solution. Finally, the degassed solution is irradiated by UV for 1 hour, resulting in the formation of an SPC sphere at least partially surrounding avidin molecule(s) attached to the inner surface of the liposome.

The lipid bilayer is removed through addition of ten parts by volume SPC-liposome solution to one part by volume 10 wt % Triton X100 solution. The addition of the Triton X100 solution also removes to a large extent the target template avidin from the SPC binding site. Triton X100 micelles incorporating the lipid material and the target template are then separated from the larger SPC particles by dialysis or centrifugation. Subsequent addition of one part 8M urea solution to one part SPC solution followed by dialysis or centrifugation removes any remaining avidin from the SPC binding sites. The SPC nanoparticle is then collected in dry form by lyophilization of the buffer solution. When resuspended in an aqueous solution, the SPC has the same dimensions as the liposome that contained it and has one or more recognition sites that map the surface of the target avidin and are thus capable of molecular recognition of avidin.

Example 2

The method as described in Example 1 is followed, but the lipids, building blocks, photoinitiators, and target template in Example 1 are substituted with any combination of the following lipids, building blocks, photoinitiators, and target templates listed below to form the SPC nanoparticle:

Lipids: A 2:2:1 weight mixture of the lipid L-phosphatidylcholine to L-phosphatidyl-ethanolamine to cholesterol.

Building blocks: Any combination of one or more of the following building block monomers: sodium acrylate, bis-acrylamido acetate (BAA), acrylamide, methylene bisacrylamide, sorbitol monoacrylate, sorbitol diacrylate, glucose monoacrylate, glucose diacrylate, acrylate-functionalized dextran.

Photoinitiators: Irgacure 907 and Darocur 1173 (Ciba Specialty Chemicals, Tarrytown, N.Y.).

Target templates: Endothelial Growth Factor Receptor (EGFR), Endothelial Growth Factor (EGF) modified by lipid anchor attachment, PspA (a *S. pneumoniae* surface protein), endotoxin.

Example 3

Synthesis of SPCs Using Protein-lipid Conjugate Amphiphiles

Preparation of Lipid Phase:

1. The lipid phase is prepared by adding phosphatidylcholine ("PC"; 33.3 mg/mL of formulation) and cholesterol (16.7 mg/mL of formulation) to a 100 mL round bottom flask. The amounts are given in terms of the final volume of aqueous phase (see Hydration of lyophilized lipid phase, below) that will be added to the dry lipid film that is obtained in Step 8. The PC is stored as a PC:chloroform stock solution. If necessary, additional chloroform may be added to help solubilize the components.

2. After all of the components have been completely dissolved, rotary evaporate the sample for 20 minutes to remove the chloroform. The result is a dry lipid film. Note that the dry lipid film contains PC and cholesterol.

3. Hydrate the lipid phase by adding 16.7 mL of 0.2 μm filtered 10 mM PBS (15 mM NaCl, pH 7.2) to the flask. Agitate the sample by placing on a shaker table or rotary mixer for 30 minutes or until a cloudy homogeneous suspension is obtained. Be sure that all of the lipids are re-suspended. It may be necessary to periodically change the orientation of the sample on the shaker/mixer to ensure re-suspension of the entire lipid/cholesterol film.

4. Add 8.3 mL of protein-hydrocarbon conjugate/surfactant (0.6 mg/mL palmitoyl-Concanavalin A ("Con A"), plus 20 mg sodium cholate/mL in 10 mM PBS (15 mM NaCl, pH 7.2)) solution to the hydrated lipids from step 3. This gives approximately 1 mg of palmitoyl-Con A per mL of formulation prepared in Hydration of lyophilized lipid phase.

5. Transfer the mixture into a 10,000 MWCO dialysis bag or cassette. Dialyze this mixture against a large volume (100–200 times the volume inside the dialysis bag or cassette) of 5–10 mM PBS (5–15 mM NaCl, pH 7.2) for at least 24 hours with frequent buffer changes (at least 4 buffer changes). This step is referred to as detergent depletion.

6. Place an empty, clean round bottom flask on the lyophilizer for a few hours. Remove the flask from the lyophilizer and tare it. After the detergent depletion is complete, remove the contents of the dialysis bag (or cassette) and transfer it to the round bottom flask.

7. Freeze the solution into a thin layer by gently rotating the round bottom in a liquid nitrogen bath. Place the flask on the lyophilizer for at least 24 hours. The sample should not be removed from the lyophilizer until it is a dry, flaky powder. If the flask is still cold or ice crystals are present, continue lyophilizing the sample.

8. After removing the flask from the lyophilizer, weigh it. Determine the total weight of lipids/protein-lipid/buffer salts in the flask by subtracting the flask-tare weight (determined in Step 6). This is the total weight of "lipid-phase".

Preparation of Osmoregulating Buffer:

The osmoregulating buffer is used during removal of extra-liposomal building blocks and initiators in the gel permeation chromatography (GPC) procedure later in this preparation procedure. The osmoregulating buffer should have close to the same osmolarity as the building block-containing aqueous phase, and it must not participate in the polymerization reaction. The osmoregulator may have a chemical structure that is not similar to the building block structure. For instance, NaCl can be used as an osmoregulator. Alternatively, the osmoregulating buffer can be made up of compounds that have chemical structures that are very similar to the building blocks, but lack polymerizable groups. In this example, glucose is used in place of glucose-2-acrylamide (G(2)Acr) and sodium acetate is used in place of sodium ornithine diacrylamide (NOD).

Prepare ~300 mL of osmoregulating buffer by mixing together glucose (6.09 g, 0.0203 mole fraction), sodium acetate (1.35 g, 0.0045 mole fraction), and phosphate buffered saline ("PBS"; 292.6 g, 0.9753 mole fraction).

Preparation of the Aqueous Phase:

The components of the aqueous phase are crosslinking building block(s), recognition building block(s) (i.e., building blocks having a moiety complementary to a target), UV-photoinitiators and buffer. The recognition building block(s) are compounds that have a specific binding interaction with the target template molecule (e.g. acryoyl-β Gal is a recognition monomer for Con A, since Con A binds to β Gal specifically through glycosylations on the surface of β Gal). The crosslinking/recognition building block(s) are polyfunctional and can be a monomer (usually bifunctional), such as BAA or dextran multi-acrylamide. Also note that the selected building blocks must be capable of being encapsulated in the interior of liposomes. Small monomers, such as acrylamide, and hydrophobic monomers, such as methylenebisacrylamide (MBA), show significant leakage from liposomes and are not suitable for this system.

Prepare the aqueous phase by mixing together, in a 20 mL glass vial, G(2)Acr (bulk monomer; 20.0 wt %), acryoyl-β Gal (recognition monomer; 0.1 wt %), NOD (crosslinking monomer; 5.0 wt %), 4,4'-azobis(4-cyanovaleric) acid ("ACVA"; initiator; 0.5 wt %), N,N,N',N'-tetramethylethylenediamine ("TMED"; initiator; 1.0 wt %), and PBS (buffer; 73.4 wt %). It is recommended to add the G(2)Acr and NOD to the vial first, followed by ACVA, then PBS, and finally TMED. It may also be beneficial to grind the ACVA into fine powder before adding it to the vial to speed its dissolution.

Acryloyl-β Gal is produced by reacting acryloyl-N hydroxysuccinimide with β-Gal. The degree of acrylation is controlled by the stoichiometry of the reactants.

Hydration of Lyophilized Lipid Phase:

Pass the aqueous solution through a 0.2 μm syringe filter into a new 20 mL vial. Calculate the amount of aqueous phase needed based on the amount of lipids obtained in Step 8 of Preparation of lipid phase, above. The desired ratio is 5 mL aqueous phase/250 mg lipid phase.

Place the sample on a shaker table or rotary mixer and allow the lipids to hydrate for 30 minutes.

While the lipids are hydrating, equilibrate a Sephadex G25 column (100 mL total volume) with 100 mL of osmoregulating buffer.

Freeze-thaw and Extrusion:

Freeze-thaw the hydrated lipid five times. One freeze-thaw cycle is: Freeze the sample by immersing the flask in liquid nitrogen for 1 minute; then thaw the sample by placing the flask in warm water (~35° C.) for a few minutes. Ensure that the sample is completely thawed before continuing.

Extrude the hydrated lipid sample through one 400 nm pore diameter (other pore sizes may be used; 400 nm is used here as an example) polycarbonate Lipex™ membrane. Use the Lipex 10 mL extruder. The first pass may require up to 200 psi for extrusion. After the first pass, replace the single 400 nm membrane with two 400 nm membranes. Extrude the sample through these double-stacked membranes ten times.

GPC to Remove Extra-liposomal Monomers:

Add 5 mL of the extruded sample onto the G25 column. Elute the liposomes with approximately 60 mL of the osmoregulating buffer. Collect the first 20 mL of eluent and discard. Begin collecting 1 mL fractions until the liposomes have been completely eluted. Transfer all of the liposome-containing fractions into a Schienk tube. The liposome fractions should have a cloudy appearance.

De-gas:
1. Hook up the Schienk tube to the N₂/water aspirator line. Pass N₂ gas into the tube and cap it.
2. With the water aspirator on, turn the T-valve from the nitrogen gas source to the vacuum.
3. Loosen the cap of the Schlenk tube and allow the vacuum to pull for 5 minutes. Turn the T-valve to N₂ again for 1 minute.
4. Return to step 2. Repeat this procedure for a total of 3 times. Tighten the cap on the Schlenk tube before removing it from the N₂/water aspirator line.

Irradiation:

Place the Schlenk tube on a rotary mixer. Irradiate the sample under a UV lamp for 30–60 minutes. The SPC-containing liposome sample is now ready for purification.

Examples 4 and 5

Other aqueous phase formulations can be used to prepare SPCs following the procedure of Example 3, including those with higher building block monomer weight percentages. The following Tables Ex.4 and Ex.5 give alternative formulations. Note, the composition of the osmoregulating buffer must be altered to match a given aqueous phase formulation.

TABLE

Ex. 4.
Aqueous Phase Formulation

| Description | Name | Weight % |
|---|---|---|
| monomer | G(2)Acr | 25 |
| Cross-linker | NOD | 7 |
| Initiator(1) | ACVA | 0.5 |
| Initiator(2) | TMED | 1.0 |
| Buffer | PBS, 10 mM | 66.5 |

TABLE

Ex. 5.
Aqueous Phase Formulation

| Description | Name | Weight % |
|---|---|---|
| monomer | G(2)Acr | 20 |
| Cross-linker | NOD | 10 |
| Initiator(1) | ACVA | 0.5 |
| Initiator(2) | TMED | 1.0 |
| Buffer | PBS, 10 mM | 68.5 |

Example 6

Synthesis of SPCs Using an Avidin-biotin DPPE Complex

Preparation of Lipid Phase:

1. The lipid phase is prepared by adding phosphatidylcholine ("PC"; 29.9 mg/mL of formulation), PEG-DPPE (11.7 mg/mL of formulation), cholesterol (16.7 mg/mL of formulation), and biotin-DPPE (0.016 mg/mL of formulation) to a 100 mL round bottom flask. The amounts are given in terms of the final volume of aqueous phase (see Hydration of lyophilized lipid phase, below) that will be added to the dry lipid film that is obtained in Step 2). The PC, PEG-DPPE and biotin-DPPE are stored as stock solutions in chloroform. If necessary, additional chloroform may be added to help solubilize the components.

2. After all of the components have been completely dissolved, rotary evaporate the sample for 20 minutes to remove the chloroform. The result is a dry lipid film. Note that the dry lipid film contains PC, PEG-DPPE, cholesterol, and biotin-DPPE, which make up the components of the lipid phase.

3. Hydrate the lipid phase by adding 5.0 mL of 0.2 μm filtered 10 mM PBS (15 mM NaCl, pH 7.2) to the flask. Agitate the sample by placing on a shaker table or rotary mixer for 30 minutes or until a cloudy homogeneous suspension is obtained. Be sure that all of the lipids are re-suspended. It may be necessary to periodically change the orientation of the sample on the shaker/mixer to ensure re-suspension of the entire lipid/cholesterol film.

4. Freeze-thaw the hydrated lipid five times. One freeze-thaw cycle is: Freeze the sample by immersing the flask in liquid nitrogen for 1 minute; then thaw the sample by placing the flask in warm water (~35° C.) for a few minutes. Ensure that the sample is completely thawed before continuing.

5. Extrude the hydrated lipid sample through one 100 nm pore diameter polycarbonate Lipex™ membrane. Use the Lipex 10 mL extruder. The first pass may require up to 600 psi for extrusion. After the first pass, replace the single 100 nm membrane with two 100 nm membranes. Extrude the sample through these double-stacked membranes ten times.

6. Add avidin (5 mg/mL) to the hydrated lipid sample. Allow the sample to incubate for 2 hours.

7. Run 1 mL of the avidin-lipid sample on the FPLC to separate non-complexed avidin from the liposomes. Use a Superdex 200-Hr-10/30 column. The liposomes with liposome-associated avidin (linked via biotin-DPPE) elute at approx. 9 min., while non-complexed avidin elutes at approx. 16 min. Other columns or methods may be used as long as there is an adequate separation of the liposome and non-complexed avidin peaks.

8. Place an empty, clean round bottom flask on the lyophilizer for a few hours. Remove the flask from the lyophilizer and tare it. Transfer all of the liposome-containing fractions to the round bottom flask.

9. Freeze the solution into a thin layer by gently rotating the round bottom in a liquid nitrogen bath. Place the flask on the lyophilizer for at least 24 hours. The sample should not be removed from the lyophilizer until it is a dry, flaky powder. If the flask is still cold or ice crystals are present, continue lyophilizing the sample.

10. After removing the flask from the lyophilizer, weigh it and subtract the flask-tare weight (determined in Step 8). This is the net weight of "lipid-phase".

Preparation of Aqueous Phase:

Following the procedure of Example 3, prepare the aqueous phase by mixing together, in a 20 mL glass vial, G(2)Acr (bulk monomer; 20.0 wt %), NOD (crosslinking monomer; 5.0 wt %), 4,4'-azobis(4-cyanovaleric) acid ("ACVA"; 0.5 wt %), N,N,N',N'-tetramethylethylenediamine ("TMED": 1.0 wt %), and PBS (buffer; 73.5 wt %).

Following the procedures of Example 3, the lyophilized lipids are hydrated with the aqueous phase, passed through five freeze-thaw cycles, and extruded. The extruded sample is then eluted through the G25 column and the liposomes collected. The liposome-containing fractions are de-gassed, and the sample is irradiated, again following Example 3 procedures, to give the SPC-containing liposomes ready for purification.

Example 7

Template Removal and Purification of SPCs

Lipid Removal:

Prepare a solvent mixture of equal parts of water, methanol, and chloroform to give 5 times the volume of the SPC-containing liposome sample to be purified. Wait until a clear phase separation occurs. The bottom phase constitutes the "lower phase", which is used as the extraction solvent.

For the extraction, to one part of SPC/liposome sample (from, e.g., Example 3, 4, 5, or 6) add one part methanol, followed by one part chloroform and vortex for 10 seconds. Centrifuge at 3000 rpm for 10 minutes. The solution separates into two layers. Remove the lower layer by aspiration and discard. Add a 1-mL aliquot of the "lower phase" solvent to the remaining upper layer of sample. Centrifuge the sample again. Repeat the extraction with the "lower phase" for a total of three times.

After the last extraction, transfer the upper layer into a round-bottom flask, and place on a rotary evaporator for 30 minutes to remove residual chloroform and methanol.

Finally, dialyze the polymer against copious amounts of distilled water with several changes over 24 hours and lyophilize to dry powder to give SPCs devoid of liposomal lipids. If it is desired to remove the target templates from the SPCs, proceed to the next steps.

Template Removal:

Obtain lipid-free samples from the lipid removal procedure describe above. The following procedure describes the removal of template from approximately 50 mg polymer). Resuspend the lyophilized polymer in 6 M urea. Vortex the suspension well to dissolve the sample, which may be viscous. The final volume will be approx. 2.5 mL.

Run the sample on an FPLC using a size exclusion column that is capable of resolving SPCs (20–1000 nm) from target template (typically under 10 nm). Transfer all pooled fractions into 50 kDa-cutoff dialysis tubing and dialyze for 6 hours against 1 liter of deionized water, with exchanges every 15 min. for the first 3 hours and then every 30 min for the second 3 hours, to remove urea.

Transfer the dialysate into a 250 mL round-bottom flask and freeze in liquid $N_2$. Lyophilize until completely dry. The resulting SPCs are devoid of the target templates.

What is claimed is:

1. A method for synthesizing a synthetic polymer complement (SPC), the method comprising:
   a) mixing together in an aqueous solution a set of building blocks, lipid constituents and water-soluble target templates, at least some of the building blocks having moieties that are complementary to moieties on the target templates;
   b) forming a liposome, wherein the building blocks of the building block set are in the interior of the liposome and the target templates are in the lipid bilayer of the liposome, wherein the building blocks contact at least a portion of the target templates;
   c) polymerizing the building blocks of the building block set that are in the interior of the liposome; and
   d) removing the lipid bilayer of the liposome to give a SPC as a crosslinked three-dimensional polymeric network comprising surface regions that are capable of binding with high affinity to at least a portion of a target.

2. A method according to claim 1, which comprises the further step of removing the target template from the SPC.

3. A method according to claim 1 wherein the set of building blocks comprises at least some building blocks consisting essentially of a crosslinking group and at least some building blocks consisting essentially of a crosslinking group and a moiety complementary to a moiety on the target.

4. A method according to claim 1 wherein the moiety complementary to the target template is selected from the group consisting of an alcohol, a carboxylic acid, an amide, an amine, a phosphate, a sulfonate, an aromatic group, a sugar, a disaccharide, and a polysaccharide.

5. A method according to claim 3 wherein the crosslinking group is selected from the group consisting of acrylate, methacrylate, acrylamide, vinyl ether, epoxide, methacrylamide, vinylbenzene, α-methylvinylbenzene, divinylbenzene, maleic acid derivative, diene, substituted diene, thiol, alcohol, amine, carboxylic acid, carboxylic anhydride, carboxylic acid halide, aldehyde, ketone, isocyanate, succinimide, carboxylic acid hydrazide, glycidyl ether, silane, siloxane, chlorosilane, alkoxysilane, alkyne, azide, 2'-pyridyldithiol, phenylglyoxal, iodo, maleimide, aryl halides, imidoester, dibromopropionate, and iodacetyl.

6. A method according to claim 3 wherein the crosslinking group is selected from the group consisting of acrylate, methacrylate, and acrylamide.

7. A method according to claim 1 wherein at least some of the building blocks comprise a sugar moiety and an acrylamide crosslinking moiety.

8. A method according to claim 1, wherein at least some of the building blocks comprise a carbohydrate moiety.

9. A method according to claim 1, wherein the target is selected from the group consisting of a peptide, a protein, a glycoprotein, a polysaccharide, a lipid, a lipopolysaccharide, an organic compound, a toxin, a pollutant, a pathogen, a synthetic drug, a steroid, a steroid derivative, a polyanion, nucleic acid, a porphyrin, a substituted porphyrin, and an active agent.

10. A method according to claim 1, wherein the SPC is capable of binding about 1 to about 10,000 targets.

11. A method according to claim 1, wherein the SPC is capable of binding about 1 to about 1000 targets.

12. A method according to claim 1, where the lipid constituents comprise lipids and at least one member selected from the group consisting of cholesterol, phosphatidyl choline, and a single-chain detergent.

13. A method according to claim 1, wherein the lipid constituents comprise lipids and (polyethylene glycol) phospholipid conjugates.

14. A method according to claim 12, wherein the lipid constituents further comprise (polyethylene glycol) phospholipid conjugates.

* * * * *